United States Patent [19]
Edebo et al.

[11] 4,417,926
[45] Nov. 29, 1983

[54] METHOD FOR CLEANING AND DISINFECTING USED PLASTIC PETRI DISHES

[75] Inventors: Lars B. Edebo, Linköping; Harald G. Swede, Malmö; Nils-Erik Tornqvist, Sigtuna, all of Sweden

[73] Assignee: Assab Medicin AB, Sundbyberg, Sweden

[21] Appl. No.: 313,349

[22] Filed: Oct. 20, 1981

[30] Foreign Application Priority Data

Oct. 20, 1980 [SE] Sweden ............................. 8007348

[51] Int. Cl.³ ............................. B08B 3/06; A61L 2/00
[52] U.S. Cl. ......................................... 134/17; 134/23; 134/25.4; 134/30; 422/38
[58] Field of Search .................... 134/17, 23, 25.4, 30; 422/25, 38, 302

[56] References Cited

U.S. PATENT DOCUMENTS

| 1,661,140 | 2/1928 | Nell et al. ............................. 422/38 |
| 2,296,974 | 9/1942 | Beal .................... 422/38 X |
| 3,725,003 | 4/1973 | Moore et al. ...................... 422/38 X |
| 3,853,622 | 12/1974 | Rutten ................................. 134/25.4 |
| 3,893,843 | 7/1975 | Fry et al. ......................... 134/25.4 X |
| 4,078,943 | 3/1978 | Saurenman ..................... 134/25.4 X |

FOREIGN PATENT DOCUMENTS

| 2729776 | 7/1979 | Fed. Rep. of Germany . |
| 2843387 | 4/1980 | Fed. Rep. of Germany ...... 422/302 |
| 1553675 | 10/1979 | United Kingdom ................ 422/302 |

Primary Examiner—Marc L. Caroff
Attorney, Agent, or Firm—Hill, Van Santen, Steadman & Simpson

[57] ABSTRACT

Contaminated plastic waste material in the form of used Petri dishes, so-called agar plates, is rendered harmless and cleaned by placing the agar plates in a bacterium-tight heating chamber maintained substantially at atmospheric pressure and contacting them with water at an elevated temperature, preferably 90°–98° C. for a predetermined period of time. After the predetermined period the agar plates are rinsed with water which is then drained off through an outlet in the bottom of the heating chamber. The agar plates to be treated are loaded into the heating chamber in batches contained in bags wholly or partly consisting of a plastic sheet material which is solid and substantially insoluble in water at room temperature but soluble in water at the elevated temperature. Invention makes use of a property of agar plates, namely that the dishes and/or lids thereof warp due to internal stresses in response to the heated water to thereby open them up in the bacterium-tight heating chamber to enable internal cleaning and rinsing.

6 Claims, 2 Drawing Figures

METHOD FOR CLEANING AND DISINFECTING USED PLASTIC PETRI DISHES

BACKGROUND OF THE INVENTION

1. Field of the Invention:

This invention relates to a method and apparatus for the rendering harmless and cleaning of infectious plastic waste material, namely, used Petri dishes made of plastic. In this context, the term "rendering harmless" is to be construed as meaning "disinfection", i.e. killing pathogenic organisms to the extent required for practical purposes.

2. Prior Art:

Petri dishes are shallow round flat-bottomed dishes of transparent material which are used for microbiological culture processes, e.g. for culturing specimens of bacteria or other microorganisms. The microorganisms are cultured on a substrate which may be in the form of sterilized agar-agar that has been heated and poured into the dish and allowed to solidify therein to form a solid flat plate; the agar-filled Petri dishes are commonly referred to as agar plates. After the specimen to be cultured has been applied to the substrate, a close-fitting lid is placed on the agar plate which is then inserted in an incubator where a controlled atmosphere is maintained. When the culturing process is completed, the cultured specimen is examined while still on the substrate.

Present-day Petri dishes are almost always produced by injection molding of plastic (clear polystyrene) and used as a disposable article. It is presumed herein that the Petri dishes are made of plastic.

Since the cultured specimens may be pathogenic, the used agar plates must be handled such that the danger of transmission of infection is minimized. The handling therefore is rather laborious. Most microbiological laboratories consume large quantities of agar plates and in some laboratories the disposal of used agar plates is more or less a full-time occupation of one person.

The disposal of used agar plates often comprises collection of the lid-bearing agar plates in bags which are closed and placed in an autoclave in which the bag is subjected to a high temperature (well above 100° C.) at elevated pressure. The bag with the now hopefully disinfected agar plates then is carried away to a refuse incinerating installation where it is burned. This way of disposing of the used agar plates not only is laborious and energy-consuming, but also leads to air pollution and destruction of valuable reusable plastic material.

SUMMARY OF THE INVENTION

The principal object of the invention is to improve the disposal of used agar plates and at the same time provide a possibility to recycle the plastic material. The problem to be solved thus is to render pathogenic organisms in or on the agar plates harmless without decomposing or otherwise destroying the plastic material and to remove the culture substrate and specimen residues.

In accordance with the invention, the agar plates are rendered harmless by heating to a temperature that is sufficient to bring about disinfection. However, in contrast to the prior art techniques, the agar plates are heated in water or other suitable fluid at a temperature below the boiling point and substantially at atmospheric pressure. In a preferred embodiment the heating serves not only to bring about disinfection and cleaning without destruction of the plastic, but also to bring about a desired but random, i.e. uncontrolled, distortion of the agar plates, including the lids, so that the interior becomes freely exposed to the water, and to liquefy the substrate (agar-agar and any added nutrient substance).

The preferred embodiment thus includes taking advantage of mechanical stresses which are accidentally or deliberately introduced in the Petri dishes during their manufacture to cause the agar plates to open themselves and thereby provide unobstructed access for the water to the interior of the agar plates so that the water can reliably effect the disinfection and the liquefaction of the culture substrate and so that the liquefied substrate can readily be washed out of the agar plates.

Heating to a temperature of about 90° C.—and sometimes even heating to only about 80° C.—is sufficient in practice (this temperature of course has to be maintained for a certain period of time to ensure killing of the pathogenic organisms to a sufficient extent), and the heating therefore can be effected in water and at atmospheric pressure. The used agar plates thus may be placed in a vessel with their lids still on and subjected to the action of hot water, preferably under agitation, for a predetermined time that is sufficient to bring about disinfection (the time is dependent on the temperature). After that, the water is drained off together with the liquefied substrate—the water may be passed into the public sewage system—and the disinfected and cleaned agar plates may then be kept and recycled without any particular measures being necessary to prevent transmission of infection.

It is preferred in carrying the invention into effect to handle the used agar plates in batches. In accordance with a preferred embodiment of the method of the invention, the used agar plates are collected in a bag which is made at least partially of a material that is solid at room temperature but soluble in water at the disinfection temperature. When the bag has been filled, it is placed in the heating vessel and subjected to the action of the hot water which thus dissolves or at least opens the bag and thus can contact the agar plates.

Available on the market are various materials which may be used for bags and which have the above-mentioned properties. One example of such a material is the plastic sheet or film material sold under the designation Kuraray Poval Film (polyvinyl alcohol film) by Kuraray Co. Ltd., Kurashiki-City, Japan, and recommended for use e.g. as a mold release agent and as a food or textile packaging material. This material is rapidly dissolved in hot water and may be allowed to go into the public sewage system.

In the above-mentioned preferred embodiment, the used agar plates may be collected in bags of a suitable size which are made wholly or partly of a material having the aforesaid properties and which are thus dissolved or at least opened when heated in water. As the bags become filled with the used agar plates, they are closed or sealed. They may then either be stored, pending transfer to the heating vessel, or immediately placed in the heating vessel to be stored there until the vessel has been filled with bags. The manual handling of the used, unprotected agar plate thereby is limited to the transit from the place of examination to the bag. The bag may suitably be small enough to make it convenient to have it at or near the place of examination so that the person making the examination can directly throw the agar plates into the bag upon completion of the examination. Thereby the danger of transmission of infection is minimized.

The method of the invention and an apparatus for carrying it into effect are described hereinafter with reference to the accompanying drawings.

DETAILED DESCRIPTION

Figure 1:
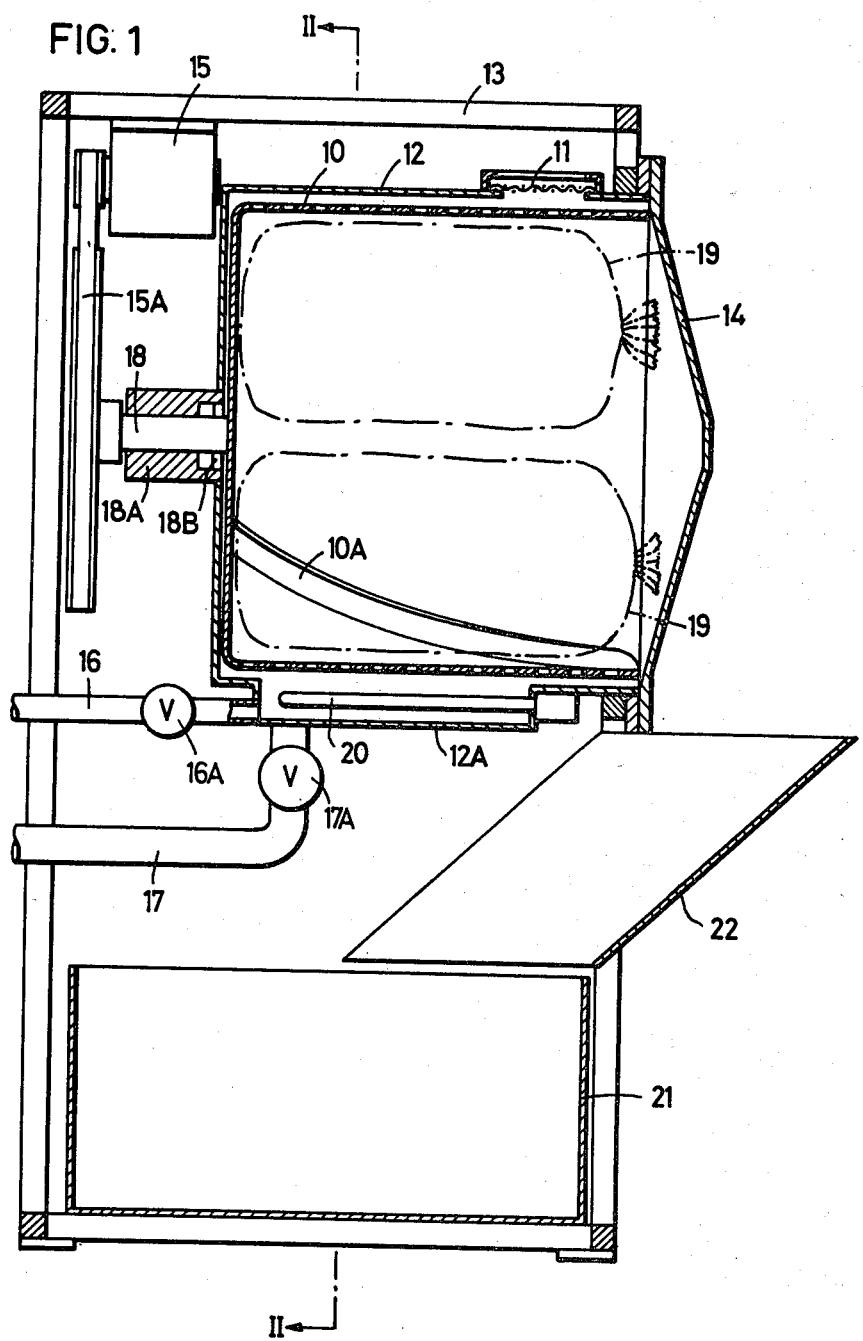
FIG. 1 is a diagrammatic view in axial cross section of a disinfecting and cleaning apparatus embodying the invention.
Figure 2:
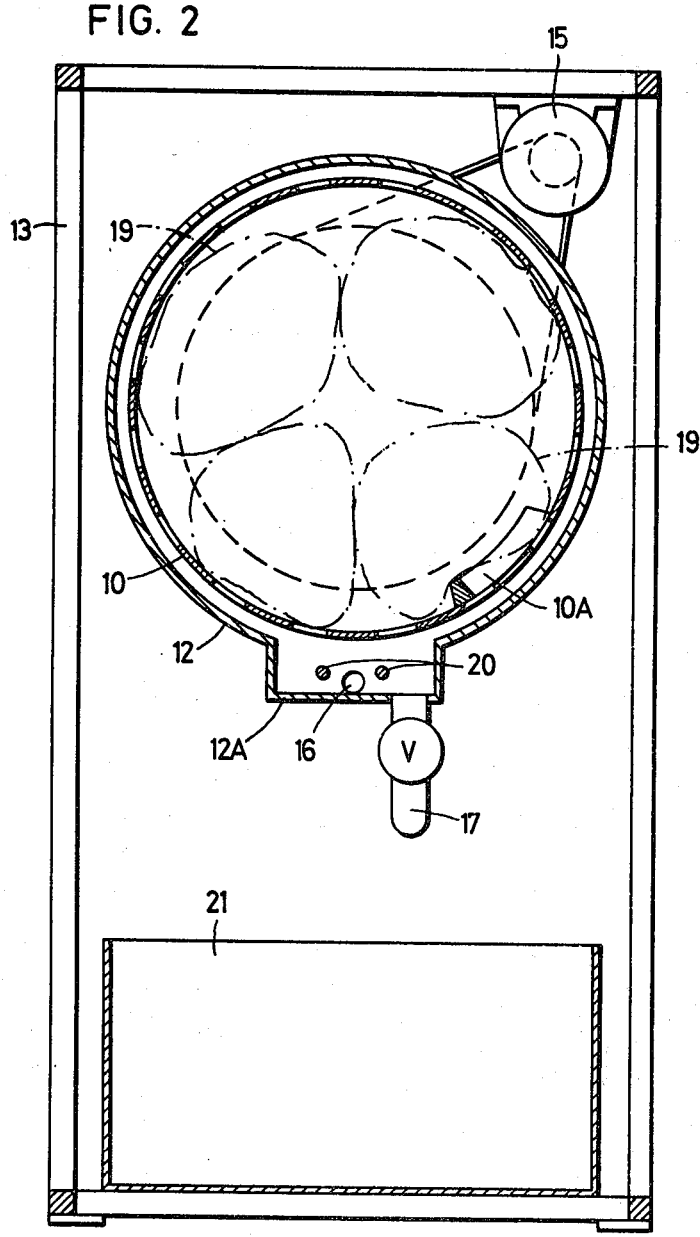
FIG. 2 is a cross-sectional view taken on line II—II of FIG. 1.

In carrying out disinfection and cleaning of used agar plates by means of the illustrated apparatus, the used agar plates are collected in bags of the afore-mentioned kind with, say, about 100 agar plates in each bag. The apparatus may be dimensioned for simultaneous disinfection and cleaning of about 400 agar plates, corresponding to four bags with 100 agar plates each. Before the filled bags are transferred to and loaded into the apparatus, they have been closed in a suitable manner, preferably through sealing or by means of a closure device made of the same water-soluble material as the bags.

The apparatus comprises a perforated cylindrical drum 10 journalled for rotation about a horizontal axis in a heating vessel 12 which is hereinafter referred to as a "housing". The housing is adapted to be closed in a bacterium-tight manner so that any bacteria present within the housing cannot escape therefrom into the surrounding atmosphere. However, even when the housing is closed, fluid communication between the interior of the housing and the surrounding atmosphere may take place by way of a bacterial filter 11. A frame 13 encloses the housing 12 and also has a charging and discharging door 14, an electric drum drive motor 15, water supply and discharge conduits 16 and 17, respectively, provided with suitable valves, as well as other elements, some of which are referred to hereinafter and some of which are omitted both from the drawings and the following description because they are not believed to be relevant to the invention.

The drum 10 is open over the entire cross-section at one end, and at the other end is secured to a shaft 18 which is rotatably supported by the housing 12 and connected with the motor 15 through a belt transmission 15A. At the point where the shaft 18 is passed through the vertical rear wall of the housing 12 and journalled in a bearing sleeve 18A attached to the housing, a seal 18B is provided to prevent water from leaking from the housing along the shaft. Moreover, means (not shown) are provided adjacent the seal which serve to lead any water accidentally leaking past the seal into a separate collecting vessel. The water may be infectious and therefore must not be allowed to escape in an uncontrolled manner from the housing. Presence of water in the collecting vessel signals that the seal is faulty and should be replaced or repaired. The circumferential wall of the drum 10 is perforated to permit virtually unrestricted fluid communication between the interior of the drum and the surrounding regions of the housing but retain the agar plates within the drum.

As shown in FIG. 1, the front wall of the housing 12 is provided with an opening in front of the open end of the drum 10. This opening, which can be closed in bacterium-tight manner by the door 14, is somewhat larger than the open end of the drum. When the door is open, the drum is thus accessible over the entire cross-section thereof to facilitate the insertion of the filled bags. The bags are shown in phantom lines at 19.

Below the drum 10, the space between the housing 12 and the circumferential wall of the drum has an enlarged region 12A in which an electrical heater 20 is provided. The water supply conduit 16, which includes a solenoid valve 16A, opens into the enlarged region 12A. The water discharge conduit 17, which likewise includes a solenoid valve 17A, is connected to the enlarged region 12A through the bottom wall of the housing. Moreover, the enlarged region houses a coiled metal tube (not shown) extending between the journal sleeve 18A and the afore-mentioned vessel for collecting any leaking water.

The operation of the disinfection and cleaning apparatus is controlled by a device that has been omitted from the drawings in the interest of clarity and is monitored by means of various safety devices which are also omitted for the just-mentioned reason.

After the bags 19 have been placed in the drum 10, the door 14 is closed whereupon the disinfection and cleaning process may be initiated. Initially, the housing 12 is filled with cold or preheated water up to a predetermined level. The water is then heated to a predetermined set temperature, e.g. 90° C., by means of the heater 20 and maintained at that temperature for a predetermined time, e.g. 30 minutes, sufficient to ensure disinfection. During this time, and possibly also during the filling of the housing with water, the drum 10 is rotated slowly in one direction by the motor 15 to cause the agar plates to tumble.

When the temperature of the water has been raised to 40°–80° C., the water dissolves the water-soluble bag material and contacts the agar plates. The consequent heating of the agar plates in many cases leads to a considerable and irregular distortion of the agar plates so that large openings are formed between the agar plates and their lids to give the water virtually unobstructed access to the interior of the agar plates. The rotation of the drum and the resulting agitation also assist in bringing the hot water into contact with every part of the agar plates. The agar substrate is melted and mixed with the water together with the residues of the cultured specimens and the dissolved bag material.

When the predetermined time has elapsed, the agar plates are washed free of the substrate and the pathogenic organisms are killed to the required extent. A predetermined quantity of additional water is then fed into the housing to lower the agar concentration and improve the washing. After a brief period of continued agitation of the agar plates and the water, the water is drained off through the discharge conduit 17 and led to the public sewage system. The rotation of the drum is continued during the draining off of the water to continue the tumbling of the now cleaned agar plates and thereby ensure that the agar plates are completely emptied of water. When the water has been drained off, pure water is again fed into the housing and the drum is rotated to ensure a thorough additional rinsing of the agar plates. The rinsing water, which need not necessarily be heated, is then drained off while the rotation of the drum is continued.

The agar plates are now rendered harmless and freed of the agar substrate. Accordingly, the door 14 may safely be opened so that the agar plates can be removed from the drum 10. The removal is effected by rotating the drum in the opposite direction. An inclined ridge 10A on the inner side of the circumferential wall of the drum assists in feeding the agar plates through the open end of the drum into a chute 22 positioned beneath the door leading to a bin 21. Alternatively, the agar plates may be discharged into a feed hopper of a mill in which they are comminuted. The now cleaned plastic material may be reused.

If the agar plates are not sufficiently clean after the above-described treatment, e.g. in view of requirements for cleanliness that have to be met to permit recycling of the plastic material, the above-mentioned rinsing step may be followed by one or more additional rinsings with cold or hot water.

The drawings show the preferred embodiment of the disinfection and cleaning apparatus. However, other embodiments are also within the scope of the invention. For example, although the illustrated horizontal disposition of the drum is believed to be preferable, it is also possible to journal the drum for rotation about a vertical axis and charge and discharge the agar plates through the top end of the drum. It may also be possible to effect agitation of the agar plates and the water in the drum in ways other than by rotating the drum.

The bacterial filter 11 may be of any suitable type available on the market. After the door 14 has been closed and sealingly engages the frame 13, the only path of fluid communication between the interior of the housing 12 and the surrounding atmosphere is formed by the bacterial filter 11. The bacterial filter 11 permits air and steam to pass relatively freely from the housing to the surrounding atmosphere but forms a barrier to bacteria. Hence, the bacterial filter 11 ensures that the interior of the housing 12 is always substantially at atmospheric pressure. The filter 11 has very fine pores and may therefore be unable to always prevent a certain overpressure to develop inside the housing as a result of the heating, but such overpressure is very small and need hardly be taken into consideration when designing the apparatus. It is proper, therefore, to regard the pressure differential between the interior of the drum and the surrounding atmosphere as a substantially zero pressure differential.

The temperature of the water should be as high as possible during the disinfection, i.e. as close to 100° C. as possible. At the same time, however, boiling of the water has to be avoided, and as a practical matter the temperature has to be kept slightly below 100° C., suitably between 90° C. and about 98° C. In the illustrated embodiment, a temperature control device (not shown) is set to keep the temperature at 95° C. so that an adequate margin to the boiling point exists. A temperature sensor (not shown) provides a warning signal if during the disinfection step the temperature should drop below the preferred lower temperature limit of 90° C.

Some types or makes of plastic Petri dishes do not have as marked a tendency as others to distort when heated in accordance with the invention. The distortion is caused by the relieving of internal stresses in the plastic material resulting from the heating. These stresses are brought about during the die-casting of the Petri dishes as the plastic material solidifies in the mold. During the actual use of the Petri dishes, the stresses are not harmful. It is therefore possible in those cases where sufficient stresses are not brought about anyway to modify the production process such that sufficiently heavy stresses are built into the Petri dishes to effect the desired distortion when the method of the invention is carried out. However, although the distortion of the agar plates is very advantageous, absence of distortion need not mean that the disinfection and cleaning will be insufficient.

Although the bags in which the used agar plates are collected may consist exclusively of a material that is soluble in hot water, it is within the scope of the invention to use bags which only partially consist of such a material. For example, the bags may be made largely of insoluble material but be provided with seams and/or closures which are dissolved by the hot water to open the bags. After completed treatment of the agar plates within the housing, the undissolved bag material can readily be separated from the disinfected and cleaned agar plates if desired or required.

We claim as our invention:

1. A method for rendering harmless and cleaning of agar plates, the plates comprising a plastic Petri dish containing an agar-based culture substrate, said method comprising the steps of:
    (a) loading batches of agar plates respectively into bag-like containers at least partly comprising a sheet material which is solid and substantially insoluble in water at room temperature but soluble in water at a predetermined temperature;
    (b) placing the loaded bag-like containers containing the batches of agar plates in a heating chamber;
    (c) closing the heating chamber in a bacterium tight manner;
    (d) feeding water into the heating chamber, the water having said predetermined temperature of at least about 80° C. but not more than 98° C. in the heating chamber, to dissolve said containers and for contacting the agar plates;
    (e) continuing said contacting for a predetermined period of time sufficient for disinfection of the agar plates while maintaining the heating chamber substantially at atmospheric pressure;
    (f) rinsing the agar plates with water; and
    (g) draining off the rinsing water through the bottom of the heating chamber, together with material washed out of the agar plates.

2. A method according to claim 1, in which said sheet material is polyvinyl alcohol.

3. A method according to claim 1, in which the agar plates are caused to tumble in the heating chamber both during said predetermined period and during the draining-off of the rinsing water.

4. A method for rendering harmless and cleaning of agar plates, the plates comprising a plastic Petri dish containing an agar-based culture substrate, said method comprising the steps of:
    (a) loading batches of agar plates covered by lids into a heating chamber;
    (b) closing the heating chamber in a bacterium tight manner;
    (c) feeding water into the heating chamber, the water having a predetermined temperature of at least about 80° C. but not more than 98° C. in the heating chamber, for contacting the agar plates;
    (d) continuing said contacting for a predetermined period of time sufficient for disinfection of the agar plates while maintaining the heating chamber substantially at atmospheric pressure;
    (e) rinsing the agar plates with water;
    (f) draining off the rinsing water through the bottom of the heating chamber, together with material washed out of the agar plates; and (g) tumbling the agar plates in the heating chamber both during said predetermined period and during said draining off of the rinsing water.

5. A method according to claim 4, in which each batch of agar plates is loaded into the heating chamber in a bag-like container at least partly comprising a sheet material which is solid and substantially insoluble in water at room temperature but soluble in water at said predetermined temperature.

6. A method according to claim 5, in which said sheet material is polyvinyl alcohol.

* * * * *